(12) United States Patent
Tang et al.

(10) Patent No.: US 9,594,028 B2
(45) Date of Patent: Mar. 14, 2017

(54) METHOD AND APPARATUS FOR DETERMINING COPLANARITY IN INTEGRATED CIRCUIT PACKAGES

(75) Inventors: Hak Wee Tang, Singapore (SG); Xulei Yang, Singapore (SG); Zin Oo Thant, Singapore (SG); Ruini Cao, Singapore (SG)

(73) Assignee: GENERIC POWER PTE LTD (SG)

(\*) Notice: Subject to any disclaimer, the term of this patent is extended or adjusted under 35 U.S.C. 154(b) by 390 days.

(21) Appl. No.: 13/997,611

(22) PCT Filed: Jul. 24, 2012

(86) PCT No.: PCT/SG2012/000267
§ 371 (c)(1),
(2), (4) Date: Jan. 30, 2014

(87) PCT Pub. No.: WO2014/017977
PCT Pub. Date: Jan. 30, 2014

(65) Prior Publication Data
US 2015/0192528 A1    Jul. 9, 2015

(51) Int. Cl.
| H04N 7/18 | (2006.01) |
| H04N 9/47 | (2006.01) |
| G01N 21/95 | (2006.01) |
| G01B 11/27 | (2006.01) |
| H01L 21/66 | (2006.01) |

(52) U.S. Cl.
CPC ....... *G01N 21/9501* (2013.01); *G01B 11/272* (2013.01); *H01L 22/12* (2013.01)

(58) Field of Classification Search
USPC ........................................................ 348/126
See application file for complete search history.

(56) References Cited

U.S. PATENT DOCUMENTS

| 6,064,756 A  * | 5/2000  | Beaty   | G06T 7/0002 250/559.23 |
| 6,630,996 B2 * | 10/2003 | Rao     | G01N 21/9501 356/237.1 |
| 7,206,080 B2 * | 4/2007  | Kochi   | G01B 11/24 348/E13.008 |
| 8,953,030 B1 * | 2/2015  | Liphardt | G01N 21/211 348/61 |

OTHER PUBLICATIONS

Wikipedia Article on "Scheimpflug principle". Publication date: Sep. 30, 2010.*

\* cited by examiner

*Primary Examiner* — Christopher S Kelley
*Assistant Examiner* — Ana Picon-Feliciano
(74) *Attorney, Agent, or Firm* — Gavrilovich, Dodd & Lindsey LLP (57) ABSTRACT

A method and apparatus for determining coplanarity of three-dimensional features on a substrate comprises a support for an object to be inspected in an object plane, a light source for illuminating the object, a first image capturing device having a first sensor and a first tiltable lens, a second image capturing device having a second sensor and a second tiltable lens, and an image processor to determine the coplanarity. Each tiltable lens is movable from a first variable angle to a second variable angle, with respect to its sensor, so that the respective lens plane and its sensor plane substantially intersect at the object plane in accordance with the Scheimpflug principle and the respective image is in focus across the whole field of view and of uniform light intensity.

11 Claims, 5 Drawing Sheets

FIGURE 1

[Prior Art]

METHOD AND APPARATUS FOR DETERMINING COPLANARITY IN INTEGRATED CIRCUIT PACKAGES

CROSS-REFERENCE TO RELATED APPLICATIONS

This United States utility patent application is the §371 national phase of PCT international patent application no. PCT/SG2012/000267, having an international filing date of Jul. 24, 2012. The aforementioned application is expressly incorporated herein by reference in its entirety and for all purposes.

FIELD OF THE INVENTION

The present invention relates to vision inspection systems. More particularly, the present invention relates to a method and apparatus for determining coplanarity of three-dimensional features in integrated circuit packages.

BACKGROUND OF THE INVENTION

In the field of miniaturized electronic circuits and integrated circuit packages, high-precision manufacturing and quality control are important. There is a need for accuracy in measurements and control of parameters for reducing defects in packaged semiconductor products, which will ultimately reduce costs associated with the process. Of particular concern is the coplanarity, or relative heights, of three-dimensional features such as solder balls in Ball Grid Array (BGA) devices or leads in Quad Flat Package (QFP) devices, which are critical to the performance of a circuit board. For example, if a solder ball has an insufficient height or is below the average height of other solder balls, there will not be any electrical connection between the solder ball and its corresponding pad on the circuit board, leading to a non-performing circuit board.

Several types of inspection apparatus have been proposed. For instance, U.S. Pat. No. 7,508,974 discloses a calibration and part inspection method for the inspection of BGA devices for measurement of heights of solder balls. Two cameras image a precision pattern mask with dot patterns deposited on a transparent reticle. The precision pattern mask is used for calibration of the system. A light source and overhead light reflective diffuser provide illumination, and a first camera images the reticle precision pattern mask from directly below. An additional mirror or prism located below the bottom plane of the reticle reflects the reticle pattern mask from a side view, through prisms or reflective surfaces, into a second camera, and a second additional mirror or prism located below the bottom plane of the reticle reflects the opposite side view of the reticle pattern mask through prisms or mirrors into the second camera. By imaging more than one dot pattern, the missing position values of the system can be resolved using a trigonometric solution. The reticle with pattern mask is removed after calibration, and the BGA device to be inspected is placed with the balls facing downward, in such a manner as to be imaged by the two cameras. The images of the BGA device are processed using a triangulation method to calculate a three-dimensional position of at least one ball with reference to a pre-calculated calibration plane.

U.S. Pat. No. 7,573,569 discloses an inspection system that combines 2-D inspection and 3-D inspection of the components of an electronic device into one compact module. The inspection system discloses a 2-D image acquisition assembly for inspecting 2-D criteria of the components, a 3-D image acquisition assembly for inspecting 3-D criteria of the components, and a computer for control and data analyzing. The 3-D image acquisition assembly comprises a 3-D image sensor and a light source. The 3-D light source is preferably a laser capable of generating a planar sheet of light that is substantially perpendicular to the inspection plane of the electronic device. The 2-D image acquisition assembly comprises a 2-D sensor and a 2-D light source positioned above the holder. The 2-D and 3-D image acquisition assemblies are arranged so that the 2-D inspection and 3-D inspection can be done while the electronic device is being held in one location.

EP Patent No. 0638801 B1 discloses a system to measure x, y, and z positional and size data of a BGA using a two camera "stereo" arrangement. One camera is used to measure the centrality of a BGA, and the other is used to sense the flatness. The flatness is measured by a tilted camera sensing crescent-shaped reflections from a light source located opposite the camera.

The above inventions suffer from limited depth of focus for the side view cameras. Some of the inspection apparatuses disclose systems made in accordance with the Scheimpflug principle. For many years, it has been known that under certain circumstances, as defined by the Scheimpflug principle, it is possible to simultaneously focus on several things at different distances from the camera, providing that all the objects of interest lie on a flat plane. Once this condition is satisfied, the object plane, the image plane, and a plane passing through the lens, all intersect along a line.

For example, U.S. Pat. No. 6,671,397 discloses a measurement system having a camera with a lens and a separate sensor mounted so that their planes intersect at an object plane in accordance with the Scheimpflug principle. A reference camera is normal and provides a two-dimensional image which is used by an image processor to determine a calibration image. This allows the image processor to determine the height of the relevant object. A single image capture provides an image of the full object, such as a BGA device. However, the image of the full object from the technique disclosed suffers from non-uniformity issues, resulting in a focused but non-uniform image, which hinders the accuracy of the results obtained.

It is, therefore, a motivation of the present invention to improve the accuracy of the measurements in vision inspection systems by producing well-focused images of uniform light intensity.

Any discussion of documents, devices, acts or knowledge in this specification is included to explain the context of the invention. It should not be taken as an admission that any of the material forms a part of the state of the art or the common general knowledge in the relevant art anywhere on or before the priority date of the disclosure and claims herein. All statements as to the date or representation as to the contents of these documents is based on the information available to applicants and does not constitute any admission as to the correctness of the date or contents of these documents.

OBJECTS OF THE INVENTION

It is an object of the invention to provide a method and apparatus of inspecting three-dimensional features in an integrated circuit module to determine whether the module meets its manufacturing specifications.

It is also an object of the invention to provide a method and apparatus for inspecting three-dimensional features in an integrated circuit module to determine the coplanarity of the three-dimensional features on a substrate in integrated circuit packages and whether the module meets its manufacturing specifications.

It is a further object of the invention to improve the accuracy of inspection systems for determining the coplanarity of three-dimensional features in an integrated circuit module.

It is a yet further object of the invention to overcome, or at least substantially ameliorate, the disadvantages and shortcomings of the prior art.

These and other objects and advantages of the present invention will become apparent from the following description, taken in connection with the accompanying drawings, wherein, by way of illustration and example, at least one embodiment of the present invention is disclosed.

SUMMARY OF THE INVENTION

According to an aspect of the invention, there is provided an apparatus for determining coplanarity of three-dimensional features on a substrate of an object. The apparatus comprises a support for the object to be inspected where the object has an object plane, a light source for illuminating the object to be inspected, a first image capturing device comprising a first sensor having a first sensor plane and a first tiltable lens having a first lens plane, the first image capturing device being mounted at a first perspective viewing angle with respect to the object plane for capturing a first side view image of the illuminated object, a second image capturing device comprising a second sensor having a second sensor plane and a second tiltable lens having a second lens plane, the second image capturing device being mounted at a second perspective viewing angle with respect to the object plane for capturing a second side view image of the illuminated object, and an image processor for processing the first and the second side view images captured by the first and the second image capturing devices to determine the coplanarity of the three-dimensional features on the substrate, wherein the first tiltable lens is movable from a first variable angle to a second variable angle, with respect to the first sensor plane, so that the first sensor plane and the first lens plane substantially intersect at the object plane in accordance with the Scheimpflug principle and the first side view image of the object is in focus across the whole field of view and of uniform light intensity, and wherein the second tiltable lens is movable from a first variable angle to a second variable angle, with respect to the second sensor plane, so that the second sensor plane and the second lens plane substantially intersect at the object plane in accordance with the Scheimpflug principle and the second side view image of the object is in focus across the whole field of view and of uniform light intensity.

According to an embodiment of the present invention, the apparatus further comprises a third image capturing device being mounted at a third perspective viewing angle which is perpendicular to the object plane for capturing a bottom view image of the object to be inspected.

According to another embodiment of the present invention, the first image capturing device and the second image capturing device are mounted symmetrically with respect to the normal of the object plane.

According to yet another embodiment of the present invention, the first image capturing device and the second image capturing device are mounted asymmetrically with respect to the normal of the object plane.

Preferably, the first sensor and the first tiltable lens are mounted on a bracket.

Preferably, the bracket holds the first sensor in a fixed position while allowing the first tiltable lens to move from a first variable angle to a second variable angle with respect to the first sensor plane.

Preferably, the first sensor is mounted at a first perspective viewing angle with respect to the object to be inspected.

Preferably, the second sensor and the second tiltable lens are mounted on a second bracket.

Preferably, the second bracket holds the second sensor in a fixed position while allowing the second tiltable lens to move from a first variable angle to a second variable angle with respect to the second sensor plane.

Preferably, the second sensor is mounted at a second perspective viewing angle with respect to the object to be inspected.

Preferably, the first sensor and the second sensor are mounted in an opposite manner such that the first sensor and the second sensor capture opposite side views of the illuminated object.

Preferably, the apparatus further comprises a pair of reflective surfaces for reflecting the object to be inspected into the first and the second image capturing devices.

According to yet another aspect of the invention, there is provided a method for determining coplanarity of three-dimensional features on a substrate in integrated circuit packages using an apparatus as described herein.

According to yet another aspect of the invention, there is provided a method for determining coplanarity of three-dimensional features on a substrate in integrated circuit packages, comprising providing an object to be inspected, capturing two or more images of the said object using two or more image capturing devices of the apparatus as described herein and processing the captured images to determine coplanarity.

This invention may also be said broadly to consist in the parts, elements, and features referred to or indicated in the specification of the application, individually or collectively, and any or all combinations of any two or more of said parts, elements, or features, and where specific integers are mentioned herein which have known equivalents in the art to which this invention relates, such known equivalents are deemed to be incorporated herein as if individually set forth.

BRIEF DESCRIPTION OF THE DRAWINGS

In order that the invention may be better understood and put into practical effect, reference will now be made to the accompanying drawings, in which.

DETAILED DESCRIPTION OF THE INVENTION

The present invention will now be described in detail in connection with preferred embodiments with reference to the accompanying drawings.

Figure 1:
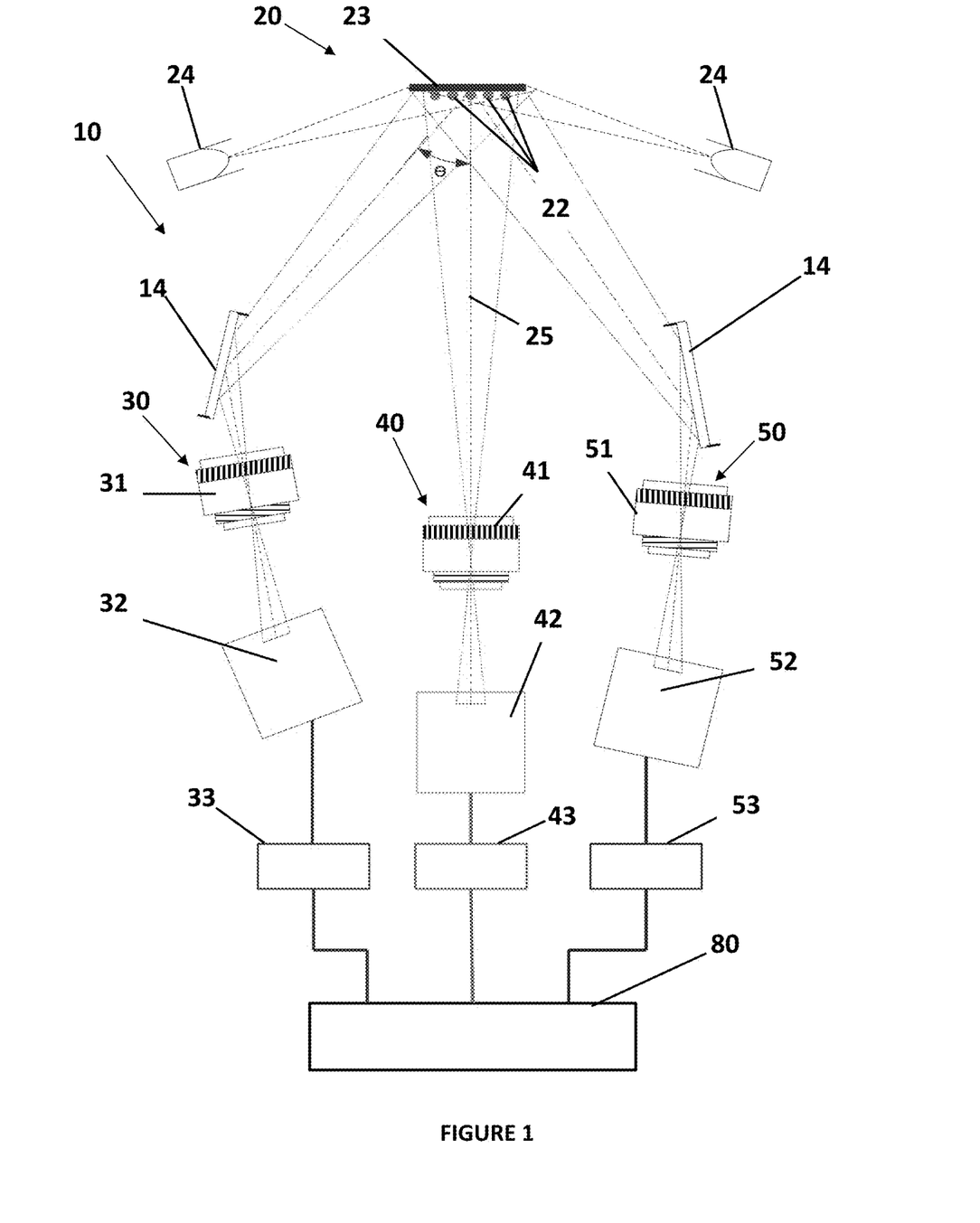
FIG. 1 is a lateral view of an apparatus of an embodiment of the present invention.

FIG. 1 represents an apparatus 10 of an embodiment of the invention for the three-dimensional inspection of BGA devices. An object 20 to be inspected is shown in FIG. 1. The object 20 comprises balls 22 positioned on a substrate 23. The object 20 to be inspected may also be a substrate with three-dimensional features such as leads in QFP devices, etc. The object 20 is supported by a robotic arm (not shown) that transports the object from point A (not shown) to point B (not shown), where point A or B may be the location where the object is inspected.

The object 20 to be inspected is illuminated with at least one light source 24. The light source 24 may be a ring light source comprising light-emitting diodes (LEDs), with their light beam emitted at an inclined angle towards the object 20 to be inspected.

The apparatus 10 may use at least two or three image capturing devices, for example, cameras, to directly image the bottom view and two side perspective views of the object 20 as shown in FIG. 1. Three cameras 30, 40, 50 are shown in the embodiment in FIG. 1. Although three cameras are shown, a configuration comprising two cameras 30, 50 is deemed workable for the purposes of performing the object of the invention. The camera 40 is mounted directly below the object 20 to be inspected, where the optical axis of the camera 40 is perpendicular to the object 20. The camera 40 includes a lens 41 and a sensor 42 located below the central area to capture a bottom view of the object 20.

The cameras 30, 50 are mounted at inclined viewing angles to the object 20 to be inspected. The cameras 30, 50 comprise a lens 31, 51 and a sensor 32, 52 respectively. Each of the cameras 30, 50 has separate lens 31, 51 and sensor 32, 52, respectively, that operate independently such that the lens is tiltable or movable with respect to the sensor to fulfill the Scheimpflug principle.

The lens 31, 51 and the sensor 32, 52 of the cameras 30, 50 are respectively held by a bracket (not shown) mounted individually on a support or stage. Each of the lens 31, 51 is tiltable with respect to the sensor 32, 52 respectively, until the object 20 to be inspected is in focus across the field of view of the cameras 30, 50. The lens 31, 51 are then locked into place with locking nuts (not shown).

The cameras 30, 40, 50 may each be electrically, electronically, or functionally connected to a frame grabber or receiver 33, 43, 53 for receiving an image. The receivers 33, 43, 53 provide image data output to an image processor 80. Preferably, the receivers 33, 43, 53 comprise an interface for transmitting images from the cameras 30, 40, 50 to the image processor 80 at a high speed. An example of a receiver useful in an embodiment of the invention is a GIGABIT™ Ethernet adapter whose function is to provide transmission of images at a speed of up to 1000 Mb/s. A GIGABIT Ethernet adapter is an interface standard introduced in 2006 for high performance industrial cameras.

The images captured by the image capturing devices are transferred through the receivers to the image processing device (not shown), which stores and processes the images. The image processing device may be an external computer operatively connected to the image capturing devices via the receivers. The image processing device comprises the image processor 80, with associated memory, and configured to obtain three-dimensional information of the object 20 to be inspected.

The Scheimpflug principle is a geometric rule that describes the orientation of the plane of focus (focus plane) of an optical imaging system when the plane of the lens (lens plane) is not parallel to the plane of the sensor (sensor plane). When an oblique tangent is extended from the sensor plane, and another is extended from the lens plane, they meet at a line through which the focus plane also passes. With this condition, a planar object that is not parallel to the sensor plane can be completely in focus when it is positioned coincidentally with the focus plane.

Figure 2A:
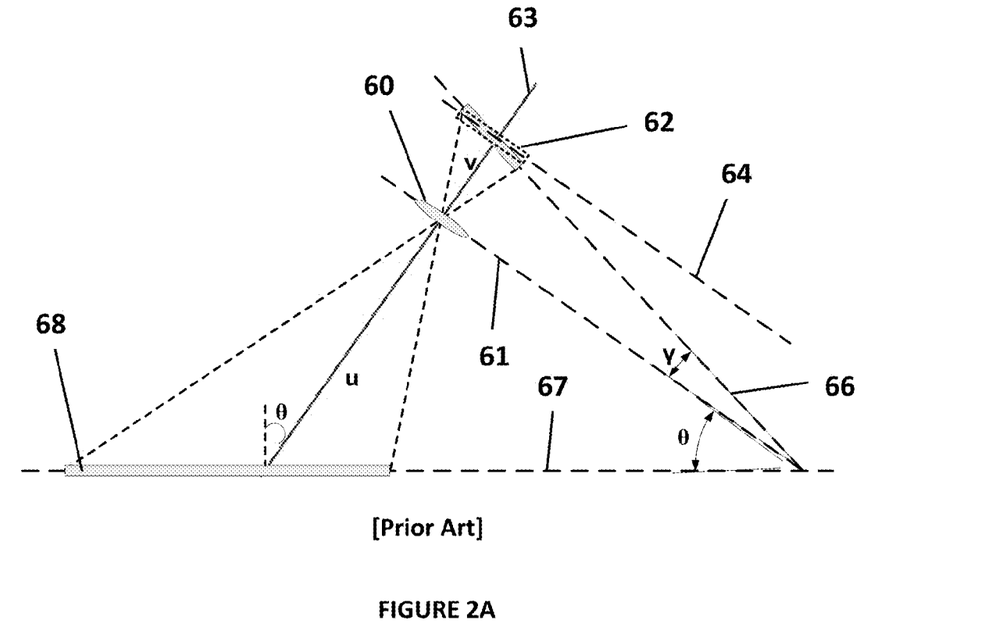
FIG. 2A is an illustration of a conventional tiltable sensor with respect to a fixed lens with a fixed viewing angle θ in accordance with the Scheimpflug principle.

Image capturing devices with tiltable sensors and fixed lens that are in accordance with the Scheimpflug principle have been used in machine vision systems to achieve better focused images by the prior art. As illustrated in FIG. 2A, the principle is implemented by tilting the sensor with respect to a fixed lens, whereby the lens has a fixed viewing angle θ to the normal of the object plane. With reference to FIG. 2A, a lens 60 has a lens plane 61, and the lens 60 is held in a fixed position. A sensor 62 is tiltable or movable within a range of angles with respect to the lens plane 61. The sensor 62, originally having a sensor plane 64 that is parallel to the lens plane 61, is tilted to a position where the sensor has a sensor plane 66. When an oblique tangent is extended from the sensor plane 66, and another oblique tangent is extended from the lens plane 61, they meet at a line through which the object plane 67 extended from a planar object 68 also passes. When this condition is met, the planar object 68 that is not parallel to the sensor plane 66 can be completely in focus. In this instance, the central line 63, i.e., the line passing through the centers of the object 68, the lens 60 and the sensor 62, is perpendicular to the lens 60. The relationship between the object plane 67, the lens plane 61, and the sensor plane 66, or the Scheimpflug principle, is embodied by the following formula:

$$\tan\gamma = \frac{f}{u-f}\tan\theta$$

$$\frac{1}{u}+\frac{1}{v}=\frac{1}{f}$$

where,
    f=effective focal length
    u=front working distance
    v=back working distance
    θ=angle between the object plane and the lens plane
    γ=angle between the lens plane and the sensor plane.

As described above, tilting the sensor to a desired orientation with respect to a fixed lens will obtain a focused image. However, for three-dimensional inspection systems of the present invention, it has been found that such an approach leads to serious problems of non-uniformity. Although the image of the object is in focus, non-uniformity of the image results in inaccurate detection of certain features on the image which are critical to determine the coplanarity. An example of the features that need to be detected on the image is the edges of the balls in BGA devices or the edges of the leads in QFP devices. Non-uniformity, when used in the context of the present invention, refers to the varying light image intensities of the image. Image intensity may refer to the amount of light reflected by a point on the object in the direction of the viewer or camera. It may also refer to the light flux per unit area or the reflected light per unit area as seen by a viewer or camera. In practice, this may refer to a focused image with varying shades of grey to black, which may hinder the detection of critical features on the image.

Figure 3A:
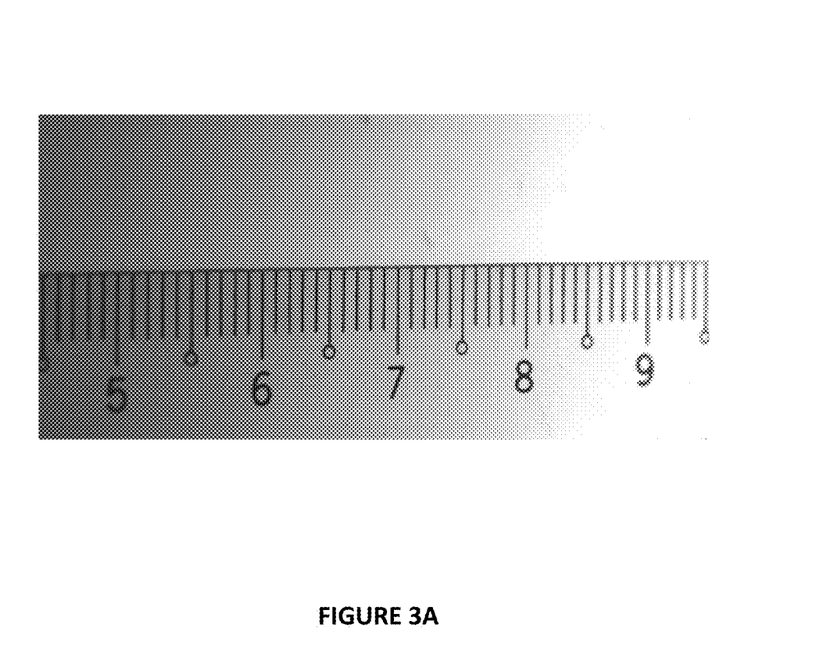
FIG. 3A represents an example of an image captured with a tiltable sensor with respect to a fixed lens in accordance with the Scheimpflug principle.

In practice, FIG. 3A shows an example of an image captured by a three-dimensional inspection system having a tiltable sensor with respect to a fixed lens satisfying the Scheimpflug principle. Although the image is in focus, it can be seen that the image suffers from non-uniform light intensities, resulting in the image having varying shades of grey. This may affect the accuracy of measurement of the vision inspection system for integrated circuit packages.

Figure 2B:
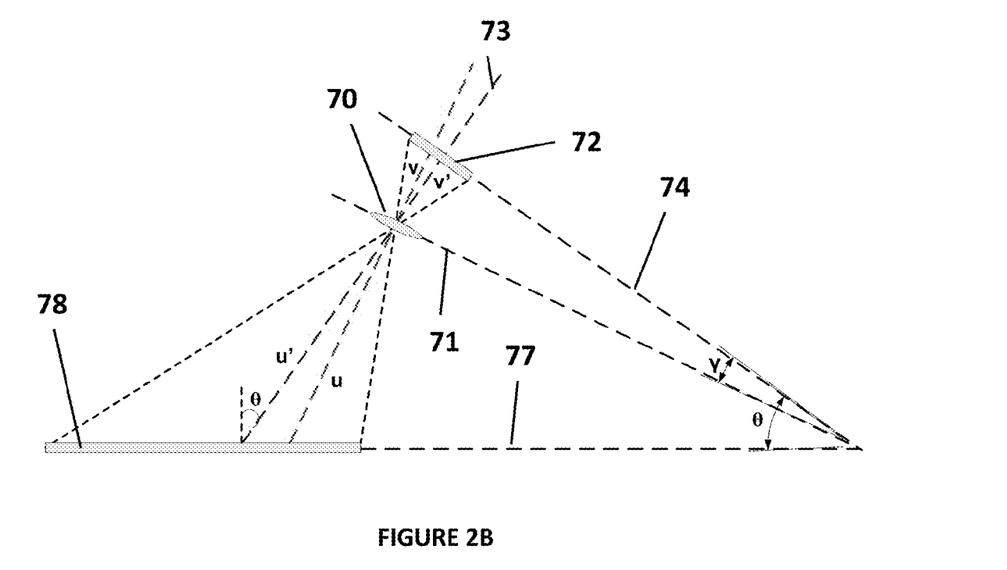
FIG. 2B is an illustration of a tiltable lens with respect to a fixed sensor with a fixed viewing angle θ in accordance with the Scheimpflug principle.

The current invention, on the other hand, implements the Scheimpflug principle by tilting the lens with respect to a fixed sensor, whereby the sensor has a fixed viewing angle θ to the normal of the object plane. As illustrated in FIG. 2B, a sensor 72 has a sensor plane 74, and the sensor 72 is held in a fixed position. A lens 70 has a lens plane 71, and the lens 70 is tiltable within a range of angles with respect to the sensor plane 74. The tiltable lens 70, originally having a lens plane (not shown) that is parallel to the sensor plane 74, is tilted to a position where the lens has a lens plane 71. When an oblique tangent is extended from the sensor plane 74, and another oblique tangent is extended from the lens plane 71, they meet at a line through which the object plane 77 extended from a planar object 78 also passes. When this condition is met, the planar object 78 that is not parallel to the sensor plane 74 can be completely in focus. In this instance, the central line 73, i.e., the line passing through the centers of the object 78, the lens 70 and the sensor 72, is perpendicular to the sensor plane 74. The relationship between the object plane 77, the lens plane 71, and the sensor plane 74, or the Scheimpflug principle, is embodied by the following formula:

$$\tan\theta = \frac{u'}{f'}\sin\gamma$$

$$\frac{1}{u'\cos\gamma} + \frac{1}{v'\cos\gamma} = \frac{1}{f'}$$

where,
f'=effective focal length
u'=distance from the center of the object to the center of the lens
v'=distance from the center of the lens to the center of the sensor
θ=angle between the object plane and the sensor plane
γ=angle between the lens plane and the sensor plane.

Figure 3B:
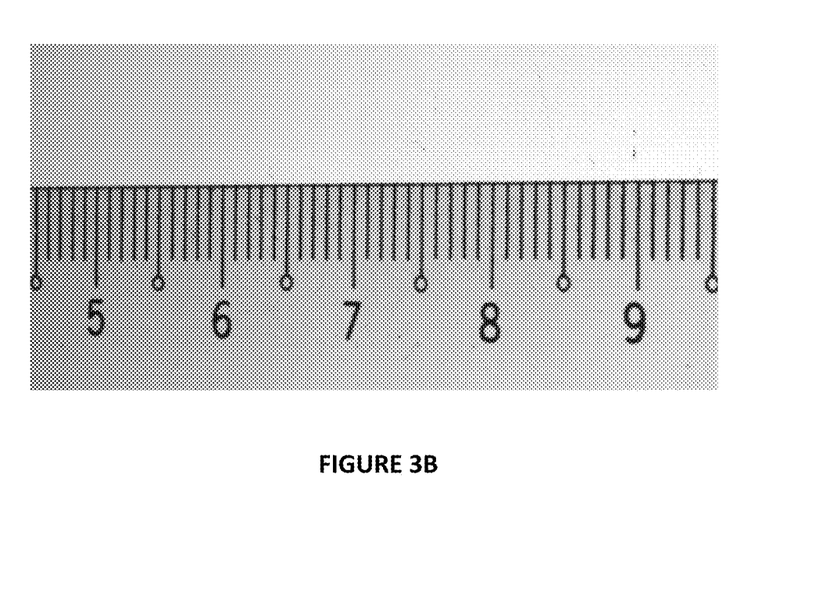
FIG. 3B represents an example of an image captured with a tiltable lens with respect to a fixed sensor in accordance with the Scheimpflug principle.

FIG. 3B represents an example of an image captured by a three-dimensional inspection system having a tiltable lens with respect to a fixed sensor satisfying the Scheimpflug principle. As it can be seen, the image is in focus and of uniform light intensity. No varying shades of light intensity are visible on the image. The accuracy of measurement of the vision inspection system is improved as the detection of features on the image of uniform light intensity is more consistent.

An embodiment of the apparatus of FIG. 1 in practice will now be explained. In operation, the image processor 80 directs the cameras 30, 50 to capture images of the object 20 to be inspected. The camera 30 will then provide a first side view image of the object 20 that is in focus across the whole field of view and of uniform light intensity. The camera 50 will provide a second side view image of the object 20 that is also in focus across the whole field of view and of uniform light intensity. The image processor 80, upon receiving the first and the second side view images, from the first and the second cameras, respectively, will be able to process the images to determine the three-dimensional information of the object 20 to be inspected. The camera 40 captures a bottom view image of the object 20 to be inspected. The image represents a two-dimensional view of the object 20 to be inspected. It is noted that other pairs of images obtained from camera 30 and camera 40, or from camera 50 and camera 40, or the three images obtained from cameras 30, 40, 50 altogether, may also be processed by the image processor 80 to obtain the three-dimensional information of the object 20 to be inspected.

Figure 4:
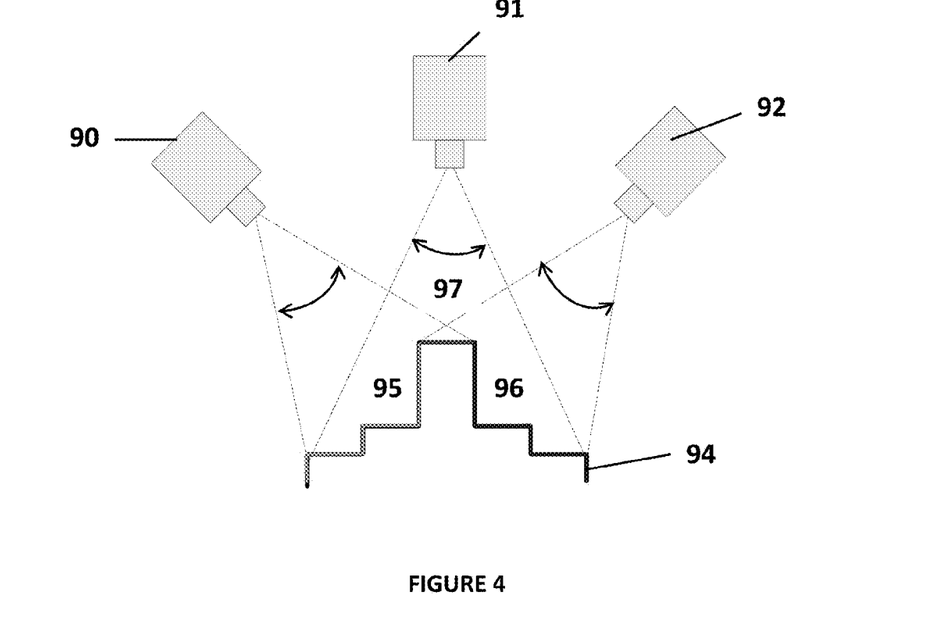
FIG. 4 represents a lateral view of an embodiment of the apparatus of the invention illustrating the varying fields of view of the image capturing devices.

Theoretically, for any stereovision inspection system, the three-dimensional information of a given point or device part may be provided by the two-dimensional information from at least two different cameras. With reference to FIG. 4 as an illustration, a left portion 95 of an object 94 can only be observed by a left side view camera 90 and a bottom view camera 91, and a right portion 96 of the object 94 can only be observed by a right side view camera 92 and the bottom view camera 91. As a result, the three-dimensional information of the left portion 95 can only be derived by using the pair of the left side view camera 90 and the bottom view camera 91, and the three-dimensional information of the right portion 96 can only be derived by using the pair of the right side view camera 92 and the bottom view camera 91. A top portion 97 of object 94, the part normal to the bottom view camera 91, can be observed by all three cameras, and the three-dimensional information for this part can be derived by any two of the three cameras or by using all three cameras. When the three-dimensional information of the left portion 95, the right portion 96, and the top portion 97 is combined together, the three-dimensional information of the whole object 94 can be provided. Therefore, with the addition of the bottom view camera 91, different sides of an object can be reconstructed. This is one of the main advantages of using camera 40. In addition, when the three-dimensional information of a part, for example, the top portion 97, is derived from all the three cameras, the three-dimensional information is more accurate than that from any two cameras. This is another main advantage of using camera 40.

With respect to FIG. 1, the central line 25 of the camera 40 is perpendicular to the plane of the object 20. The angle θ denotes the perspective viewing angle of one of the cameras 30, 50. Theoretically, the viewing angle θ may be any value within the range (0, 90). In practice, the viewing angles of the cameras 30, 50 are selected in such a way that for BGA devices, the tip of the ball (ball tip) or a point close to the ball tip should be perceivable on the side view images, and for QFP devices, the neighboring leads are distinguishable on the side view images. In a preferred embodiment, the viewing angle would have a range from 25° to 40°. The cameras 30, 50 may also be configured or arranged symmetrically or asymmetrically about the central line 25.

To make the apparatus more compact, reflective surfaces or mirrors 14 may be used to reflect the rays from the object into the cameras. Preferably, the mirrors 14 are placed at inclined angles with respect to the object 20 in such a manner that the whole object 20 lie within the field of view and be captured by the cameras.

In order to derive the three-dimensional information of the object to be inspected, calibration of the cameras is important. In particular, the internal camera parameters of individual cameras and the spatial relationship or relative poses (positions and orientations) between the cameras are critical. The image processor utilizes the HALCON® multi-view calibration technique, which may involve two or more cameras (see, Solution Guide III-C, 3D Vision, Version 10.0, incorporated herein by reference, software available from MVTec Software GmbH of Munich, Germany). The multi-view calibration method calibrates all the cameras at the same time and forms a common three-dimensional coordinate system (camera setup coordinate system) for reference. This means that whichever pair of the cameras, or whichever triple of the cameras, is used to derive the three-dimensional information for different parts of the object, the three-dimensional information is at the same coordinate system. Therefore, the three-dimensional information from different parts of the object can be combined directly to reconstruct the three-dimensional world for the whole object.

A calibration grid comprising a border and an array of precision dots is presented to the cameras in various poses within the field of view of the cameras. At each pose, a set of multi-view images (multi-view image set) of the calibration grid is captured by the cameras. At least ten out of these multi-view image sets are selected for the calibration process. The selected multi-view image sets should cover the whole field of view of the cameras.

During calibration, the vision system reads the multi-view image sets in sequence to locate the dots within the borders. The precise spatial relationships among the dots on the calibration grid are used to compute the internal camera parameters of individual cameras and the relative poses between the cameras. The resulting parameters are saved as a so-called camera setup model.

The image points from a multi-view image set that originate from the same object point are referred to as conjugate points. From the principle of stereovision, given the image locations of the conjugate points and the camera setup model, the three-dimensional location of the object point in the camera setup coordinate system can be computed.

For a BGA device, the main task is to detect the conjugate points for each ball in the multi-view image set. One wants to select a point in each image in the multi-view image set that can be detected consistently to form the conjugate points. Ideally, the point can be the ball tip, which is the highest point on the ball. In practice, the true ball tip may not be easily detected on the image. However, the selected point can be made close enough to the true ball tip by using proper lighting and camera viewing angles. In each image in the multi-view image set, edge detection is first performed to detect the boundaries of the device, and within these boundaries standard blob analysis is performed to locate the gross position of each ball. Two edge detection windows are then projected onto each ball to locate its top and bottom edge locations up to sub-pixel accuracy. From these two edges, a third edge detection window is projected, centered vertically, to detect the right edge of the ball in the left side view image, the center of the ball in the bottom view image if the bottom view camera is used, and the left edge of the ball in the right side view image up to sub-pixel accuracy. These detected edge points of one ball in the multi-view image set form its conjugate points. The image coordinates of these conjugate points, together with the camera setup model are used to derive the three-dimensional location of the ball tip in the camera setup coordinate system. And the three-dimensional locations of the ball tips are further used to determine the coplanarity of the balls in BGA devices as described below.

To determine the coplanarity of the three-dimensional features on the substrate, a hypothetical surface (reference surface) is constructed, from which the distance from each of the three-dimensional features to the reference surface is measured. The simplest surface to develop is a plane (reference plane), but more general surfaces, such as parabolic, elliptical, and other higher order surfaces, can be used.

Figure 5A:
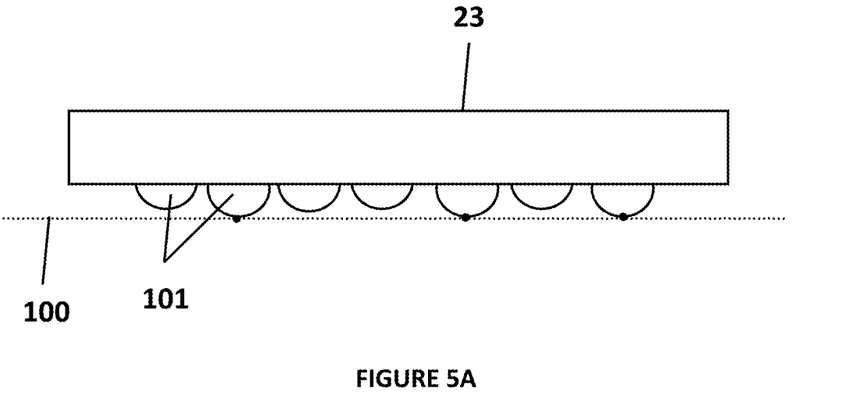
FIG. 5A is an illustration of the seating plane method for determining coplanarity in integrated circuit packages.

While many techniques are available for determining the reference plane, one that is commonly used is the seating plane method. The seating plane method yields a surface from the three-dimensional locations of the ball tips, with all the balls lying on one side of the surface. As shown in FIG. 5A, the substrate 23 is oriented with the balls 101 resting on a seating plane 100. The seating plane 100 is defined by at least three or more of the balls resting on the seating plane 100. The coplanarity of each ball, using this method, is the distance from the tip of the ball to the seating plane 100.

Figure 5B:
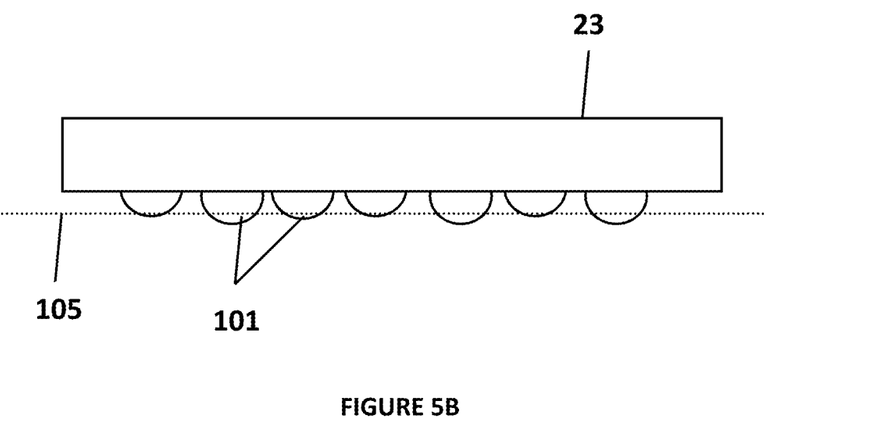
FIG. 5B is an illustration of the regression plane method for determining coplanarity in integrated circuit packages.

A second method for determining the reference plane that is also commonly used is known as the regression plane method. As shown in FIG. 5B, this method is based on the least mean square regression analysis. The analysis yields a best fit surface plane (regression plane) 105 from the three-dimensional locations of the ball tips, in which some of the balls lie above and others lie below the plane. The coplanarity of each ball, using this method, is the distance from the tip of the ball to the regression plane 105 or to a shifted regression plane.

The present invention makes use of both methods to determine the coplanarity of three-dimensional features on a substrate.

The present invention has been described above with the aid of functional building blocks illustrating the implementation of specific functions and relationships thereof. The boundaries of these functional building blocks have been arbitrarily defined herein for the convenience of the detailed description. Alternative boundaries can be defined so long as the specific functions and relationships thereof are appropriately performed.

Although the invention has been herein shown and described in what is conceived to be the most practical and preferred embodiment, it is recognized that departures can be made within the scope of the invention, which is not to be limited to the details described herein but is to be accorded the full scope of the appended claims so as to embrace any and all equivalent devices and apparatus.

"Comprises/comprising" when used in this specification is taken to specify the presence of stated features, integers, steps or components but does not preclude the presence or addition of one or more other features, integers, steps, components or groups thereof.

The invention claimed is:

1. An apparatus for determining coplanarity of three-dimensional features on a substrate of an object, comprising:
   a support for the object to be inspected where the object has an object plane;
   a light source for illuminating the object to be inspected;
   a first image capturing device comprising a first sensor having a first sensor plane and a first tiltable lens having a first lens plane, the first image capturing device being mounted at a first perspective viewing angle with respect to the object plane for capturing a first side view image of the illuminated object,
   wherein the first sensor and the first tiltable lens are mounted on a first bracket that holds the first sensor in a fixed position while allowing the first tiltable lens to move from a first variable angle to a second variable angle with respect to the first sensor plane;

a second image capturing device comprising a second sensor having a second sensor plane and a second tiltable lens having a second lens plane, the second image capturing device being mounted at a second perspective viewing angle with respect to the object plane for capturing a second side view image of the illuminated object, wherein the second sensor and the second tiltable lens are mounted on a second bracket that holds the second sensor in a fixed position while allowing the second tiltable lens to move from a first variable angle to a second variable angle with respect to the second sensor plane;

an image processor for processing the first and the second side view images captured by the first and the second imaging capturing devices to determine the coplanarity of the three-dimensional features on the substrate, wherein the first tiltable lens is movable with respect to the first sensor plane, so that the first sensor plane and the first lens plane substantially intersect at the object plane in accordance with the Scheimpflug principle and a first central line that passes from the center of the object, through the center of the first lens and the center of the first sensor is perpendicular to the first sensor plane, and wherein the second tiltable lens is movable with respect to the second sensor plane, so that the second sensor plane and the second lens plane substantially intersect at the object plane in accordance with the Scheimpflug principle and a second central line that passes from the center of the object, through the center of the second lens and the center of the second sensor is perpendicular to the second sensor plane.

2. The apparatus according to claim 1, further comprising a third image capturing device being mounted at a third perspective viewing angle which is perpendicular to the object plane for capturing a bottom view image of the object to be inspected.

3. The apparatus according to claim 1, wherein the first image capturing device and the second image capturing device are mounted symmetrically with respect to the normal of the object plane.

4. The apparatus according to claim 1, wherein the first image capturing device and the second image capturing device are mounted asymmetrically with respect to the normal of the object plane.

5. The apparatus according to claim 1, wherein the first sensor is mounted at a first perspective viewing angle with respect to the object to be inspected.

6. The apparatus according to claim 1, wherein the second sensor is mounted at a second perspective viewing angle with respect to the object to be inspected.

7. The apparatus according to claim 1, the first sensor and the second sensor are mounted in an opposite manner such that the first sensor and the second sensor capture opposite side views of the illuminated object.

8. The apparatus according to claim 1, further comprising a pair of reflective surfaces for reflecting the object to be inspected into the first and the second image capturing devices.

9. A method for determining coplanarity of three-5 dimensional features on a substrate in integrated circuit packages using an apparatus of claim 1.

10. A method for determining coplanarity of three-dimensional features on a substrate in integrated circuit packages, comprising:
providing an object to be inspected;
capturing two or more images of said object using two or more image capturing devices of an apparatus of claim 1; and
processing the captured images to determine coplanarity.

11. An apparatus for determining coplanarity of three-dimensional features on a substrate of an object, comprising:
a support for the object to be inspected where the object has an object plane;
a light source for illuminating the object to be inspected;
a first image capturing device comprising a first sensor having a first sensor plane and a first tiltable lens having a first lens plane, the first image capturing device being mounted at a first perspective viewing angle with respect to the object plane for capturing a first side view image of the illuminated object,
wherein the first sensor and the first tiltable lens are mounted on a first bracket that holds the first sensor in a fixed position while allowing the first tiltable lens to move from a first variable anile to a second variable anile with respect to the first sensor plane;
a second image capturing device mounted at a second perspective viewing angle which is perpendicular to the object plane for capturing a bottom view image of the illuminated object; and
an image processor for processing the first and the second view images captured by the first and the second imaging capturing devices to determine the coplanarity of the three-dimensional features on the substrate,
wherein the first tiltable lens is movable from a first variable angle to a second variable angle, with respect to the first sensor plane, so that the first sensor plane and the first lens plane substantially intersect at the object plane in accordance with the Scheimpflug principle and wherein a central line that passes from the center of the object, through the center of the first tiltable lens and the center of the first sensor is perpendicular to the sensor plane.

* * * * *